(12) United States Patent
Depernet et al.

(10) Patent No.: US 6,462,227 B2
(45) Date of Patent: Oct. 8, 2002

(54) STABILIZED O-IODOXYBENZOIC ACID COMPOSITIONS AND PROCESS FOR THE PREPARATION THEREOF

(75) Inventors: Dominique Depernet, La Rochelle (FR); Bruno Francois, Saint Martin de Re (FR)

(73) Assignee: Simafex, Marans (FR)

( * ) Notice: Subject to any disclaimer, the term of this patent is extended or adjusted under 35 U.S.C. 154(b) by 0 days.

(21) Appl. No.: 10/050,035

(22) Filed: Jan. 17, 2002

(65) Prior Publication Data

US 2002/0107416 A1 Aug. 8, 2002

(30) Foreign Application Priority Data

Jan. 19, 2001 (FR) .............................. 01 00759

(51) Int. Cl.⁷ .................. C07F 13/00; C07C 63/26; C07C 63/06; C07C 63/04; C07C 53/126
(52) U.S. Cl. .................. 560/400; 560/493; 570/264
(58) Field of Search ................ 562/400, 493; 570/264

(56) References Cited

U.S. PATENT DOCUMENTS 2,566,592 A 9/1951 Aschner

*Primary Examiner*—Brian J. Davis
(74) *Attorney, Agent, or Firm*—Jacobson Holman, PLLC

(57) ABSTRACT

Compositions that comprise, for one mole of o-iodoxybenzoic acid, from 0.5 to 4 moles of an aliphatic acid of formula $CH_3(CH_2)_nCOOH$, in which n is from 8 to 20, of a benzenecarboxylic acid of formula

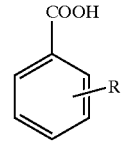

in which R represents H, $CH_3$, COOH or of mixtures thereof.

18 Claims, No Drawings

STABILIZED O-IODOXYBENZOIC ACID COMPOSITIONS AND PROCESS FOR THE PREPARATION THEREOF

BACKGROUND OF THE INVENTION

The invention relates to stabilized o-iodoxybenzoic acid, or IBX, compositions of the formula

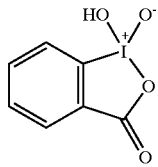

and to a process for the preparation thereof.

DESCRIPTION OF PRIOR ART

This hypervalent iodine derivative is the precursor of 1,1,1-triacetoxy-1,1-dihydro-1,2-benzodioxol-3(1H)-one or periodinane of Dess-martin, of the Formula

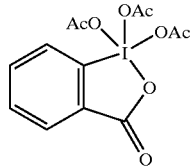

which was described for the first time in J. org. Chem. 1983, 48, 4155–4156 as a gentle and selective oxidizer of primary and secondary alcohols into carbonyl compounds.

Despite that important property, the risks run during the handling of that reagent and its precursor, IBX, hinder their marketing and even their use in chemical synthesis, beyond the laboratory stage.

Those two compounds decompose violently, as mentioned by J. B. Plumb and D. J. Harper in Chemical, and Engineering News, p3, Jul. 16, 1990 or in J. Org. Chem. 1993, 58, 2899, which article describes an improved process for the preparation of Dess-Martin periodinane starting from IBX.

IBX can be prepared by oxidizing 2-iodobenzoic acid, especially with $KBrO_3$ in sulfuric acid, this being a usual process which has been improved several times, or with Oxone®, consisting of $2KHSO_5, KHSO_4, K_2SO_4$, as described in J. Org. Chem. 1999, 64, 4537–4538. The authors of this recent article confirm that the IBX obtained is a white crystalline solid which explodes even when in very pure form.

The applicant has himself established that Dess-Martin periodinane decomposes violently at its melting temperature and that IBX, even when moistened with water or acetic acid, has explosive properties when it is subjected to the action of heat in accordance with method A14 of Directive 92/69/EEC.

It was therefore desirable to find a means of stabilizing o-iodoxybenzoic acid as soon as it has been prepared in order to enable it to be used in organic synthesis without major risk.

Sorbitol, which was proposed 50 years ago in U.S. Pat. No. 2,566,592 as an agent for stabilizing IBX and its calcium and ammonium salts in order to permit their use in therapeutics, does not really appear to be efficient and, above all, it is not suitable when IBX has to be used in a reaction for oxidizing alcohols.

The applicant has now found other agents for stabilizing IBX which do not hinder its use as an oxidizing agent, and the composition comprising a suitable amount of at least one of those agents and IBX no longer explodes under the action of impact or a major increase in temperature, so that this periodinane can be used more widely in synthesis, especially instead of the Dess-Martin reagent.

M. Frigerio, M. Santogostino, S. Sputore and G. Palmisano have reported in J. Org. Chem. 1995, 60, 7272–7276 that IBX, whose insolubility in numerous organic solvents and in water limited its use, had, in solution in dimethyl sulfoxide, oxidizing properties comparable to those of the Dess-Martin reagent, without exhibiting the latter's sensitivity to moisture which was reported, in particular, in J. Org. Chem. 1994, 59, 7549–7552.

By way of example of that use, there may be mentioned in addition to the reactions described by M. Frigerio et al. those resulting from the work of K. C. Nicolaou et al., which is described, in particular, in Angew. Chemie, Int. Ed. 2000, 39, 625–628 and 2525–2529 or, in the case of anilides, in Angew. Chemie 2000, 112(3), 639–642.

It has now been found that those reactions could be carried out in polar aprotic solvents other than dimethyl sulfoxide when using the stabilized compositions of the invention, especially in tetrahydrofuran or N-methylpyrrolidone.

SUMMARY OF THE INVENTION

The present invention relates to stabilized o-iodoxybenzoic acid compositions that comprise, for one mole of o-iodoxybenzoic acid, from 0.5 to 4 moles of a stabilizing agent selected from the group consisting of:

aliphatic acids of formula I

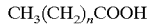

$CH_3(CH_2)_n COOH$ in which n is from 8 to 20 and preferably equal to 14 or 16, and mixtures thereof, benzenecarboxylic acids of formula II

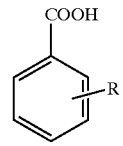

in which R represents H, $CH_2$, COOH and mixtures thereof and mixtures of acids of formula I and II.

Preference is given to compositions in which there are from 1 to 2.5 moles of stabilizing agent per mole of o-iodoxybenzoic acid and especially from 1.8 to 2.2 moles, in order to ensure maximum stabilisation without increasing costs excessively.

Of the acids of formula II, preference is given to benzoic, toluic, isophthalic and terephthalic acids and, of those, to the acids having melting points higher than 200° C., such as isophthalic acid and terephthalic acid, which temperature is generally acknowledged to be that at which IBX explodes spontaneously.

However, mixtures of benzoic acid or o-toluic acid or a mixture thereof, on the one hand, and of isophthalic acid or terephthalic acid or a mixture thereof, on the other hand, at the rate of from 25 to 75 mole % of the monoacid in the mixture and preferably from 45 to 55%, give stabilized compositions that do not explode under the action of impact or heat.

Iodoxybenzoic acid compositions comprising one or more compounds of formula II as the stabilizing agent are preferred.

It is preferable in compositions based on a stabilizing agent of formula I also to introduce an agent of formula II and preference is given to mixtures of, on the one hand, stearic acid or palmitic acid or a mixture thereof, which are widely available acids, and, on the other hand, terephthalic acid or isophthalic acid or a mixture thereof, at the rate of from 25 to 75 mole t of fatty acid in the mixture.

The invention relates also to the process for the preparation of the compositions of the invention, either starting from IBX that has already been isolated or during the synthesis of IBX.

In order to prepare a composition starting from IBX that has already been isolated or in order to homogenise a composition of the invention, a solution or suspension in water of the alkali salts, particularly of sodium, of the acids constituting the composition is prepared and then the solution or suspension is acidified until the composition has been rendered completely insoluble.

It is possible either to add a solution of an alkali hydroxide to the suspension of the component acids in water or to add said acids to an aqueous alkali hydroxide solution in a sufficient amount.

It is also possible to introduce preferably all or part of a suitable amount of one of the stabilizing agents of formula I or II, one of its alkali salts or a mixture thereof into the medium in which the IBX is prepared, as soon as the reaction starts, if the stabilizing agent is not decomposed in that reaction medium. When the stabilizing agent is a mixture, one of the components can be added in the course of the reaction and the other can be added before the IBX is isolated.

The person skilled in the art can determine in a few preliminary tests the relative proportions of the stabilizing agent(s) and of IBX and also the methods of introducing those agents, taking into account their possible reactivity and their relative solubilities in the reaction and precipitation media.

DESCRIPTION OF EXAMPLES

Examples of the invention and their application as oxidizing agents are described hereinafter.

The concentration of IBX in the compositions obtained was determined by quantitative analysis with sodium thiosulfate of the iodine released during the oxidation of KI by the IBX present in the composition (oxidimetric test).

The explosivity tests were carried out in a laboratory:
- either by subjecting 100 mg of a composition to the impact of a hammer
- or by spraying a few mg of composition onto a plate heated to 300° C. or by heating a plate on which a few mg have been deposited until decomposition occurs.

Example 1 a) Preparation of IBX.

300 g of 2-iodobenzoic acid are suspended in 3 l of water containing 201 g of 96% $H_2SO_4$. Then, while agitating at 50° C., 246 g of $NaBrO_3$ in 1.2 l of water are introduced over a period of 30 minutes. The medium is then maintained at 65° C. for 3 hours 30 minutes, in the course of which strong evolution of bromine occurs. After cooling to 20° C., the IBX precipitated in the medium is carefully isolated, washed with 1 l of water and dried under vacuum.

Yield: 95%

100 mg of that powder subjected to impact give rise to a strong evolution of smoke; on a hot-plate, the powder explodes with an orange flash and a strong evolution of smoke.

b) 10 g of IBX are suspended in 60 ml of water, and 2.2 g of benzoic acid (0.5 molar equivalent) are added before the slow introduction, with agitation, of approximately 6 ml of aqeous 10N NaOH solution, until dissolution is complete. The medium is then slowly acidified by the addition of 6 ml of an aqueous 33% HCl solution. The precipitate formed is isolated by filtration, washed with 30 ml of water and dried at 60° C. under vacuum.

Yield by weight: 90%

A composition is obtained which, when heated, gives a thick grey smoke but no orange flame.

Example 2

30 g of 2-iodobenzoic acid are introduced into a solution of 109 g of Oxone in 390 ml of water. The heterogeneous reaction medium is maintained under agitation at 70° C. for 2 hours in the course of which it thickens 18 g of benzoic acid are then added and the mixture is left to cool to ambient temperature, approximately 20° C. The precipitate is isolated, washed with 100 ml of water and dried under vacuum at 60° C.

Yield: 90%

The composition obtained, which comprises 1.2 mole of stabilizing agent per mole of IBX, is stable to impact and heating in the usual tests; it decomposes while producing a grey smoke but no orange flame when the heat test is carried out with 500 mg.

Example 3

30 g of 2-iodobenzoic acid are introduced into a solution of 92 g of Oxone in 300 ml of water. After 2 hours at 70° C., 18 g of o-toluic acid are added and the medium, which has returned to 20° C., is filtered. After washing the solid with 100 ml of water and drying, a powder is obtained which is decomposed by heat without exploding.

Example 4

50 g of 2-iodobenzoic acid and 37 g of isophthalic acid are added to a solution of 153 g of Oxone in 500 ml of water The heterogeneous medium is maintained at 70° C. for 2 hours and then it is cooled to ambient temperature before being filtered. The precipitate is washed with water then suspended in 800 ml of water before the addition of approximately 60 ml of an aqueous 10N NaOH solution, in order to dissolve the acids. An homogenised composition according to the invention is then precipitated by acidifying the medium by the addition of 60 ml of an aqueous 33% HCl solution. After washing with water and drying, 80 g of a stable composition which does not explode as a result of an increase in temperature but melts while turning black are obtained.

Example 5

10 g of stearic acid are added to a suspension of 10 g of IBX in 60 ml of water before the dropwise introduction of 8 ml of aqueous 10N NaOH solution in order to produce the salts of the acids. The heterogeneous medium is then acidified by the addition of 8 ml of an aqueous 33% HCl solution before isolating the solid phase by filtration. The composition obtained after washing with 30 ml of water and drying does not explode when exposed to heat.

Example 6

32 g of 2-iodobenzoic acid and 32 g of stearic acid are introduced into a solution of 117 g of Oxone and 490 ml of water. After 2 hours at 70° C., the medium is treated as above; the isolated composition generally does not explode when exposed to heat.

Example 7

280 g of 2-iodobenzoic acid, 187 g of isophthalic acid and 151 g of benzoic acid are introduced into 1014 g of Oxone in 4600 ml of water. After 2 hours at 70° C. and the usual treatment, 605 g of a composition which is stable when heated and which comprises 46% by weight of IBX, determined by oxidimetry, are isolated.

Example 8

The same proportions of reagents as in the previous Example are used but the benzoic acid and the isophthalic acid are not introduced until after oxidation in the course of cooling the medium to approximately 35° C. The composition isolated by filtration is then homogenised. It is suspended in 4100 ml of water, and 440 ml of aqueous 10N NaOH solution are added; the solution obtained, having a pH of 7, is then acidified at 78° C. by the slow addition of 440 ml of an aqueous 33% hydrochloric acid solution. The composition isolated after filtration, washing with 500 ml of water and drying under vacuum comprises 45% by weight of IBX (oxidimetry). It is stable to impact and does not explode as a result of being heated.

Example 9

The procedure is as in Example 8 but the benzoic acid is replaced by one molar equivalent of stearic acid. A nonexplosive composition comprising 38% by weight of IBX is thus obtained.

Example 10

200 g of o-iodobenzoic acid and 133 g of isophthalic acid are introduced into a solution of 695 g of Oxone in 2.8 litres of water. The medium is maintained under agitation at 70° C. for 3 hours and then a solution of 128 g of sodium benzoate in 500 ml of water is added thereto at 40° C. After cooling to 20° C., the precipitate is filtered off, washed with 700 ml of water and dried in a ventilated over at 60° C. to obtain 420 g of stabilized IBX composition.

Application Example No. 1

5 g of the composition prepared in Example 7 are introduced in small fractions over a period of 15 minutes into a solution of 1.6 g of farnesol in 40 ml of dimethyl sulfoxide while maintaining the temperature at from 20° C. to 25° C. After 2 hours under agitation, the solution is poured into 100 ml of hexanes (petrol G) and the precipitate is separated off and washed with water and then with petrol G. The organic phases are concentrated under vacuum and the residue obtained is purified by chromatography over 25 g of R60 Merck® silica in order to separate the remaining stabilizing agent from the farnesal obtained; the eluent is petrol G and then its mixture with ethyl acetate (9/1-v/v). The pure farnesal is isolated with a yield of 85%.

Application Example No. 2 a) In Dimethyl Sulfoxide

While the temperature is maintained at from 2° C. to 25° C., 16 g of the composition prepared as in Example 8 are added in small fractions over a period of 15 minutes to 35 ml of dimethyl sulfoxide containing 4.8 g of benzoin. After 2 hours, agitation at ambient temperature, the medium is poured into 200 ml of water and 60 ml of ethyl acetate. The precipitate formed is eliminated and the organic phase is concentrated under vacuum. The solid residue is recrystallised from 20 ml of ethanol. Benzil is obtained with a yield of 78%.

b) In Tetrahydrofuran 8.35 g of stabilized composition prepared as in Example 10 are added in small fractions to a solution of 2.5 g of benzoin in 40 ml of tetrahydrofuran at 20° C. and then the mixture is agitated at 50° C. for 6 hours. At 20° C., the medium is introduced, with agitation, into 100 ml of water and 60 ml of toluene; the aqueous phase is then neutralised by the addition of a 5N NaOH solution, the insoluble portion is filtered off and the organic phase is separated off. After washing with 60 ml of water and evaporation of the solvent, 2 g of the expected diketone are obtained (according to NMR spectrum).

c) In N-methylpyrrolidone

The reaction is carried out in the same manner as in tetrahydrofuran to obtain, after treatment, 2.6 g of the expected product.

Application Example No. 3

30.6 g of the composition of Example 10 are added in small fractions over a period of 15 minutes and while maintaining the temperature at approximately 20° C. to a solution of 4.7 g of 3-pyridylmethanol in 70 ml of dimethyl sulfoxide and the medium is agitated for 2 hours before pouring it into 150 ml of water and 60 ml of ethyl acetate After neutralisation of the aqueous phase and separation of the precipitate, the organic phase is separated off and brought to dryness. 4.2 g or the expected 3-pyridylcarboxaldehyde are obtained (according to NMR)

Application Example No. 4

10.6 g of stabilized IBX prepared as in Example 10 are suspended in 60 ml of N-methylpyrrolidone at 20° C., and 2 g of cyclooctanol are added dropwise while maintaining the temperature at from 20° C. to 25° C. After 2 hours, agitation, the medium is poured into a mixture of 130 ml of water and 80 ml of toluene; the pH of the aqueous phase is brought to approximately 7 by the addition of aqueous NaOH and the organic phase, after separation of the insoluble material formed and of the aqueous phase, is concentrated to give 1.4 g of pure cyclooctanone (NMR and GPC)

Application Example No. 5

By applying the same operating mode as before, menthone is obtained from L-menthol with a yield of 87%.

Application Example No. 6

By applying the operating mode of Example 4, 3,4,5-trimethoxybenzaldehyde is obtained with a yield of 86% from 3,4,5-trimethoxybenzyl alcohol or adamantanone is obtained with a yield of 52% from adamantanol.

What is claimed is:

1. Stabilized o-iodoxybenzoic acid composition that comprises, for one mole of o-iodoxybenzoic acid, from 0.5 to 4 moles of a stabilizing agent selected from the group consisting of aliphatic acids of formula I

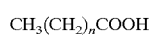

in which n is from 8 to 20 benzenecarboxylic acids of formula II

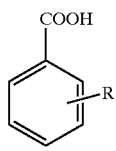

in which R represents H, CH$_2$, COOH and mixtures thereof.

2. Composition according to claim 1, in which the stabilizing agent is an acid of formula in which n is equal to 14 or 16 or a mixture thereof.

3. Composition according to claim 1, in which the stabilizing agent is an acid of formula II or a mixture of acids of formula II.

4. Composition according to claim 1, in which the stabilizing agent is isophthalic acid, terephthalic acid or a mixture thereof.

5. Composition according to claim 1, in which the stabilizing agent is a mixture of benzoic acid or o-toluic acid or a mixture thereof, on the one hand, and of isophthalic acid, terephthalic acid or a mixture thereof, on the other hand, at the rate of from 25 to 75 mole % of monoacid in the stabilizing agent.

6. Composition according to claim 1, in which the stabilizing agent is a mixture of benzoic acid and isophthalic acid at the rate of from 45 to 55 mole % of monoacid in the stabilizing agent.

7. Composition according to claim 1, in which the stabilizing agent is a mixture of stearic acid, palmitic acid or a mixture thereof, on the one hand, and of isophthalic acid, terephthalic acid or a mixture thereof, on the other hand, at the rate of from 25 to 75 mole % of monoacid in the stabilizing agent.

8. Composition according to claim 1, which comprises from 1 to 2.5 moles of stabilizing agent per mole of o-iodoxybenzoic acid.

9. Process for the preparation of a composition according to claim 1, which consists in making an aqueous solution or suspension of the alkali salts of o-iodoxybenzoic acid and of the stabilizing agent in suitable proportions, and then in acidifying before isolating the precipitated composition.

10. Process for the preparation of a stabilized o-iodoxybenzoic acid composition according to claim 1, which consists in introducing the stabilizing agent or one of its alkali salts into the reaction medium for the synthesis of o-iodoxybenzoic acid.

11. Process according to claim 10, in which the o-iodoxybenzoic acid is prepared by the action of 2KHSO$_5$, KHSO$_4$, K$_2$SO$_4$ on o-iodobenzoic acid.

12. Process according to claim 10, in which the o-iodoxybenzoic acid is prepared by the action of NaBrO$_3$ and H$_2$SO$_4$ on o-iodobenzoic acid.

13. Composition according to claim 2, which comprises from 1 to 2.5 moles of stabilizing agent per mole of o-iodoxybenzoic acid.

14. Composition according to claim 3, which comprises from 1 to 2.5 moles of stabilizing agent per mole of o-iodoxybenzoic acid.

15. Composition according to claim 4, which comprises from 1 to 2.5 moles of stabilizing agent per mole of o-iodoxybenzoic acid.

16. Composition according to claim 5, which comprises from 1 to 2.5 moles of stabilizing agent per mole or o-iodoxybenzoic acid.

17. Composition according to claim 6, which comprises from 1 to 2.5 moles of stabilizing agent per mole of o-iodoxybenzoic acid.

18. Composition according to claim, 7, which comprises from 1 to 2.5 moles of stabilizing agent per mole of o-iodoxybenzoic acid.

* * * * *